US012691047B2

(12) United States Patent
Shah

(10) Patent No.: US 12,691,047 B2
(45) Date of Patent: Jul. 28, 2026

(54) PERSONAL CARE COMPOSITION

(71) Applicant: FINE ORGANIC INDUSTRIES LIMITED, Mumbai (IN)

(72) Inventor: Jayen Shah, Mumbai (IN)

(73) Assignee: FINE ORGANIC INDUSTRIES LIMITED, Mumbai (IN)

( * ) Notice: Subject to any disclaimer, the term of this patent is extended or adjusted under 35 U.S.C. 154(b) by 1068 days.

(21) Appl. No.: 17/910,244

(22) PCT Filed: Aug. 4, 2020

(86) PCT No.: PCT/IN2020/050689
§ 371 (c)(1),
(2) Date: Sep. 8, 2022

(87) PCT Pub. No.: WO2021/024274
PCT Pub. Date: Feb. 11, 2021

(65) Prior Publication Data
US 2023/0111799 A1 Apr. 13, 2023

(30) Foreign Application Priority Data
Aug. 5, 2019 (IN) .............................. 201921031568

(51) Int. Cl.
| | |
|---|---|
| *A61K 8/92* | (2006.01) |
| *A61K 8/36* | (2006.01) |
| *A61K 8/365* | (2006.01) |
| *A61K 8/39* | (2006.01) |
| *A61Q 5/00* | (2006.01) |
| *A61Q 19/00* | (2006.01) |

(52) U.S. Cl.
CPC ................ *A61K 8/39* (2013.01); *A61K 8/361* (2013.01); *A61K 8/365* (2013.01); *A61K 2800/10* (2013.01); *A61K 2800/34* (2013.01); *A61K 2800/805* (2013.01)

(58) Field of Classification Search
CPC .......... A61K 8/39; A61K 8/361; A61K 8/365; A61K 2800/10; A61K 2800/34; A61K 2800/805
See application file for complete search history.

(56) References Cited

U.S. PATENT DOCUMENTS

| | | | | |
|---|---|---|---|---|
| 3,636,017 | A | 1/1972 | Eng | |
| 7,629,479 | B2 * | 12/2009 | Kondo .................... | C07C 69/33 |
| | | | | 554/227 |
| 2002/0035238 | A1 * | 3/2002 | Nakamura ............. | C08G 65/34 |
| | | | | 528/425 |
| 2007/0092470 | A1 | 4/2007 | Allef et al. | |
| 2012/0181056 | A1 | 7/2012 | Chaudhary et al. | |
| 2015/0315123 | A1 * | 11/2015 | Schuch .................. | C07C 69/52 |
| | | | | 554/173 |
| 2017/0071836 | A1 | 3/2017 | Schelges et al. | |
| 2019/0202771 | A1 * | 7/2019 | Von Hof .................. | A61K 8/39 |
| 2019/0209442 | A1 | 7/2019 | Syed et al. | |

FOREIGN PATENT DOCUMENTS

| | | | | |
|---|---|---|---|---|
| CN | 101161802 | A | 4/2008 | |
| CN | 106588648 | A * | 4/2017 ............. | C07C 67/08 |
| JP | 2007074990 | A | 3/2007 | |
| JP | 2013056858 | A | 3/2013 | |

OTHER PUBLICATIONS

English Translation CN106588648A Polyglycerol-lactic acid-fatty acid ester used as emulsifier and preparation method thereof (Year: 2017).*
Polyglyceryl Esters—http://cyberlipid.gerli.com/description/simple-lipids/polyglyceryl-esters; download: Oct. 30, 2020.
International Search Report dated Nov. 10, 2020, Application No. PCT/IN2020/050689.
Supplementary European Search Report issued by the European Patent Office in European Patent Applciation No. 20 85 0903, dated Aug. 11, 2023.

* cited by examiner

*Primary Examiner* — Sahana S Kaup
*Assistant Examiner* — Toriana N. Vigil
(74) *Attorney, Agent, or Firm* — ArentFox Schiff LLP

(57) ABSTRACT

A personal care composition and its process of preparation wherein the composition comprises (a) polyglycerol ester product of 5 weight parts of lactic acid, 5 weight parts of lauric acid and 90 weight parts of polyglycerol; (b) one or more ingredient(s) and (c) water; wherein the polyglycerol is with an average polymeric degree of 2-5.

11 Claims, No Drawings

PERSONAL CARE COMPOSITION

CROSS-REFERENCE TO RELATED APPLICATIONS

This application is a National Phase of PCT Application No. PCT/IN2020/050689, filed Aug. 4, 2020, which claims the benefit of Indian Application No. 201921031568, filed Aug. 5, 2019, the disclosures of each of which are hereby incorporated by reference in their entireties.

The present invention relates to a personal care composition, its process of preparation and use in the cosmetic industry.

BACKGROUND OF THE INVENTION

U.S. Pat. No. 3,636,017 (assigned to M/s Glyco Chemicals Inc, referred to herein as '017) discloses use of lactylic acid esters of fatty acids as additives for bakery products. However, the present invention suggests a personal care composition comprising a polyglycerolester product and its use.

United States Patent Application Publication number 2017/0071836 (applicant M/w Henkel AG, referred to herein as '836) exemplifies use of fatty acyl lactylates as cosmetic cleansing agents. However, the present invention prepares a personal care composition comprising a polyglycerol ester product and its use.

Chinese Patent application No. 106588648 discloses preparation of polyglycerol esters wherein the polyglycerol is a tetramer. However, it suggests use of the polyglycerol esters as moisturizers. The present invention prepares a personal care composition comprising a polyglycerol ester and its use in various personal care compositions such as shampoos, face washes and the like.

OBJECT OF THE INVENTION

The object of the present invention is to provide a personal care composition with a polyglycerol ester product, its process of preparation and use as shampoo, scalp cleanser, hair cleanser, shower preparations, shower gels, foam baths, gels, body wash, facial cleanser, face wash, makeup remover, cleansing wipe, sunscreen, foundation and the like.

Another object of the present invention is to provide sulfate, ethylene oxide, amide, silicone free personal care composition with pH of 3 to 5.

SUMMARY OF THE INVENTION

A personal care composition comprising
(a) polyglycerolester product of 5 weight parts of lactic acid, 5 weight parts of lauric acid and 90 weight parts of polyglycerol;
(b) one or more ingredient(s) and
(c) water;
wherein the polyglycerol is with an average polymeric degree of 2-5.

DESCRIPTION OF THE INVENTION

Mild personal care compositions with stable emulsions are in demand by consumers.

It is known that sulfates in personal care compositions may damage cells and strip away natural oils and hair proteins & ethanolamide based surfactants may comprise nitroso compounds which are considered harmful when in contact with skin.

In view of the same we have developed a personal care composition which is stable and mild. The personal care composition of the present invention is user friendly as it is sulfate free, amide free, ethylene oxide free, silicone free, paraben free and formaldehyde free.

According to one embodiment of the present invention is the personal care composition comprising polyglycerolester product of 5 parts of lactic acid, 5 parts of lauric acid and 90 parts of polyglycerol; one or more ingredient(s) and water; wherein the polyglycerol is with an average polymeric degree of 2-5.

Typically, the personal care composition of the present invention will comprise 5 to 50% by weight polyglycerolester product, 5 to 50% by weight of one or more ingredient(s) and 10 to 90% by weight water.

The polyglycerol ester product used in the personal care composition of the present invention comprises 5 parts by weight of lactic acid, 5 parts by weight of lauric acid and 90 parts by weight of polyglycerol; wherein the polyglycerol is with an average polymeric degree of 2-5.

The polyglycerol used to prepare polyglycerol ester product is a mixture of mainly diglycerol, triglycerol, tetraglycerol and pentaglycerol. Typically, the polyglyerol comprises 20-40% by weight of diglycerol, 30-50% by weight of triglycerol, 5-15% by weight of tetraglycerol and 2-5% by weight pentaglycerol.

Typically, the average molecular weight of the polyglycerol used to prepare the polyglycerol ester product used in the personal care composition of the present invention is 180-250 gms.

It is well known in the art that surfactants with HLB values greater than 10 are hydrophilic and will help in solubilization. The polyglycerol ester product used in the personal care composition of the present invention imparts HLB value of 15-20 rendering it hydrophilic properties useful in solubilizing other ingredients used in the composition.

The polyglycerol ester product used in the personal care composition of the present invention has hydroxyl value of 900 to 1200 mg/KOH/gm.

The personal care composition comprises ingredients typically used in personal care compositions to enhance the properties useful to the end user such as feel, fragrance, appearance, flowability, emulsion stability, ease in handling and the like. The ingredients may be selected from anionic, cationic, zwiterrionic, nonionic, amphoteric surfactants; superfatting agents, stabilizers, biogenic active ingredients, humectants, preservatives, pearlizing agents, dyes and pigments, fragrances, solvents, opacifiers, further thickeners and dispersants, protein derivatives such as gelatin, collagen hydrolysates, polypeptides, fatty alcohols, odor masking agents and enzymes.

The personal care composition further comprises water as a vehicle.

The personal care composition of the present invention provide stable emulsions and demonstrate better foaming properties and is mild to human skin and hair as it is sulfate, ethylene oxide, amide, silicone free personal care composition with pH of 3 to 5.

The personal care composition of the present invention is with pH of 3 to 5 which helps in maintaining stability of the emulsion form of the composition.

The personal care composition of the present invention is used as shampoo, scalp cleanser, hair cleanser, shower preparations, showergels, foam baths, gels, body wash, facial cleanser, face wash, makeup remover, cleansing wipe, sunscreen, foundation and the like.

The personal care composition of the present invention is tested for Counter irritancy using Semi-occlusive patch test and found to be satisfactory even in combination with commonly used irritating surfactants like sodium laureth sulfate.

According to second embodiment of the present invention is the process for the preparation of polyglycerolester product used in the personal care composition. The process for the preparation of the polyglycerol ester product comprises reacting polyglycerol with lauric acid and lactic acid at temperature ranging from 150 to 250° C. under inert atmosphere. The progress of the reaction is monitored by acid value. The reaction is terminated when the acid value may be between 1 to 2 mg KOH/g. The reaction mixture cooled and worked up.

The polyglycerol used to prepare polyglycerol ester product is a mixture of mainly diglycerol, triglycerol, tetraglycerol and pentaglycerol. Typically, the polyglyerol comprises 20-40% by weight of diglycerol, 30-50% by weight of triglycerol, 5-15% by weight of tetraglycerol and 2-5% by weight pentaglycerol.

Typically, the average molecular weight of the polyglycerol used to prepare the polyglycerolester product used in the personal care composition of the present invention is 180-250 gms.

The mole ratio of polyglycerol:lauric acid:lactic acid may be between 8:0.5:0.5 to 12:2:2.

According to yet another embodiment of the present invention is the process for the preparation of the personal

EXAMPLES

Example 1: Preparation of Polyglyerol Ester Product (Polyglyceryl Lauroyl Lactylate)

Polyglycerol (2070 gm/9.7 mole) is added to a clean round bottom flask fitted with a stirrer, sparger for Nitrogen gas bubbling and temperature probe. The round bottom flask is heated to 75° C. under gentle nitrogen flow to provide inert atmosphere and lauric acid (115 gm/0.58 mole) is added. Once the mass appears homogeneous lactic acid (130 gm/1.28 mole) is added. The temperature of the reaction mixture is raised under stirring to 220° C. The progress of the reaction is monitored by acid value of the reaction and when it reaches ~1.5 mg KOH/g, the reaction is terminated by lowering the temp to ~100° C., residual water evacuated under vacuum, the reaction mass is filtered and the polyglycerolated product analysed. Yield 2230 g.

Example 2: Physico—Chemical Data of the Polyglycerol Ester Product of Example 1

| Test | Results |
| --- | --- |
| Description | Viscous yellow liquid |
| Acid value | 1.4 mg KOH/g |
| Sap value | 42 mg KOH/g |
| Hydroxylvalue | 991 mg KOH/g |
| Soap content | 0.89% |

Example 3: Hair Cleansing Composition of the Present Invention

| Ingredient | INCI* | 1 % (w/w) | 2 % (w/w) |
| --- | --- | --- | --- |
| Deionized Water | Deionized Water | 50.95 | 50.95 |
| Disodium EDTA | Disodium EDTA | 0.10 | 0.10 |
| Methocel 40-101 | Hydroypropyl Methylcellulose | 2.00 | 2.00 |
| Iselux LQ-CLR-SB | Sodium Lauroyl Methyl Isethionate | x | 20.00 |
| Chembetain CGF | Cocamidopropyl Betaine | x | 10.00 |
| Finester 2009 | Polyglyceryl Lauroyl Lactylate | 40.00 | 10.00 |
| Finester 6128 | complex ester comprising Diglycerine; 12-Hydroxystearic acid, C8-C10 Acid; Stearic Acid; Isostearic Acid and Adipic Acid | 1.00 | 1.00 |
| Finamul 97 | Sodium Stearoyl-2-Lactylate | 2.00 | 2.00 |
| Finester EG 2010 | Ethylene Glycol Diste arate | 1.50 | 1.50 |
| D-Panthenol | Panthenol | 1.00 | 1.00 |
| Sodium Benzoate | Sodium Benzoate | 0.20 | 0.20 |
| Potassium Sorbate | Potassium Sorbate | 0.10 | 0.10 |
| Euxyl PE 9010 | Phenoxyethanol and Ethyl Hexyl Glycerin | 1.00 | 1.00 |
| Citric Acid Anh. | Citric Acid | 0.15 | 0.15 |
| | | 100.00 | 100.00 | care composition comprising mixing polyglycerol ester product and ingredient(s) in water as a vehicle. The process may comprise heating the polyglycerol ester product and/or ingredients in water to enable dissolution followed by cooling.

The following examples illustrate preferred embodiments in accordance with the present invention without limiting the scope of the invention.

Procedure:

To the main vessel add deionized water. Dissolve disodium EDTA and disperse Methocel 40-101 with rapid mixing in the deionized water. Heat to 60° C. and reduce mixer speed. Add Iselux LQ-CLR-SB, Chembetain CGF, Finester 2009, Finester 6128, Finamul 97, Finester EG 2010 and maintain the temperature to 60° C. Mix until uniform. Cool to 40° C. and add remaining ingredients. Mix until uniform, while cooling to room temperature.

Example 4: Conditioning Shampoo of the Present Invention PLLAIS-7 Series

| Ingredient | INCI* | % (w/w) |
|---|---|---|
| Deionized Water | Deionized Water | 53.50 |
| Disodium EDTA | Disodium EDTA | 0.10 |
| Methocel 40-101 | Hydroypropyl Methylcellulose | 1.00 |
| Jagual C17 | Guar Hydroxypropyltrimoniyum Chloride | 0.20 |
| Nansa LSS 38/AV | Sodium C14-16 Olefin Sulfonate | 20.00 |
| Chembetain CGF | Cocamidopropyl Betaine | 10.00 |
| Finester 2009 | Polyglyceryl Lauroyl Lactylate | 10.00 |
| Finamul 97 | Sodium Stearoyl-2-Lactylate | 2.00 |
| D-Panthenol | Panthenol | 1.00 |
| Sodium Benzoate | Sodium Benzoate | 0.20 |
| Potassium Sorbate | Potassium Sorbate | 0.10 |
| Euxyl PE 9010 | Phenoxyethanol and Ethyl Hexyl Glycerin | 1.00 |
| Citric Acid Anh. | Citric Acid | 0.90 |
| TOTAL | | 100.00 |
| | pH | 4.01 |
| | Viscosity (cps) Brookfield DVLVII+, 6 rpm, TF 1 min helipath on | 26869 |

Example 5: Personal Care Compositions of the Present Invention

(a) Antiseptic Wipes

| Ingredient | INCI* | % (ww) |
|---|---|---|
| Deionized Water | Deionized Water | 93.76 |
| Finester 2009 | Polyglycerol Lauroyl Lactylate | 5.00 |
| Fragrance | Perfume | qs |
| Benzethonium Chloride | Benzethonium Chloride | 0.24 |
| Diocide | Phenoxyethanol, Caprylyl Glycol, Hexylene Glycol | 1.00 |
| Total | | 100.00 |

Weigh water in main vessel and dissolve benzethonium chloride. Premix remaining ingredients until clear and uniform and add to main vessel to prepare a solution. Saturate non-woven wipes with the solution.

(b) Gentle Make-Up Remover

| Ingredient | INCI* | % (ww) |
|---|---|---|
| Deionized Water | Deionized Water | 79.00 |
| Methocel 40-0101 PCG | Hydroxypropyl Methyl Cellulose | 1.00 |
| Finester 2009 | Polyglycerol Lauroyl Lactylate | 20.00 |
| Fragrance | Parfum | qs |
| Diocide | Phenoxyethanol, Caprylyl Glycol, Hexylene Glycol | 1.00 |

Weigh water in main vessel. Disperse Methocel under rapid mixing. Premix remaining ingredients until clear and uniform and add to main vessel.

(c) Mineral Sunscreen

| Ingredient | INCI* | % (ww) |
|---|---|---|
| Deionized Water | Deionized Water | 40.50 |
| Glycerin | Glycerin | 3.00 |

-continued

(c) Mineral Sunscreen

| Ingredient | INCI* | % (ww) |
|---|---|---|
| Butylene Glycol | Butylene Glycol | 5.00 |
| Keltrol CG-T | Xanthan Gum | 0.50 |
| Eumulgin SG | Sodium Stearoyl Glutamate | 1.00 |
| Caprylic/Capric Triglyceride | Caprylic/Capric Triglyceride | 8.00 |
| Finsolv TN | C12-15 Alkyl Benzoate | 8.00 |
| Diisopropyl Adipate | Diisopropyl Adipate | 5.00 |
| Finester 2009 | Polyglycerol Lauroyl Lactylate | 5.00 |
| Finester LAN-S | Glyceryl Hydroxystearate, Glyceryl Adipate, Glyceryl Stearate | 3.00 |
| Z-Cote HP1 | Zinc Oxide (and) Triethoxycaprylylsilane | 20.00 |
| Fragrance | Perfume | qs |
| Diocide | Phenoxyethanol, Caprylyl Glycol, Hexylene Glycol | 1.00 |
| Total: | | 100.00 |

Weigh water in main vessel, dissolve glycerin and butylene Glycol, disperse Keltrol CG-T. When the mixture is uniform disperse Eumulgin SG. Heat to 80° C. until uniform, then cool to 40° C.

Combine Caprylic/Capric Triglyceride, Finsolv TN, Diisopropyl Adipate, Finester 2009, Finester LAN-S, Z-Cote in auxiliary vessel. Heat to 60-70° C. and homogenize to disperse. Cool to 40° C. Mix and then add this mixture to main vessel.

Homogenize to emulsify, when uniform add fragrance and diocide under regular mixing.

(d) High Coverage SPF Foundation

| Ingredient | INCI* | % (ww) |
|---|---|---|
| Deionized Water | | 37.75 |
| 1,3 Butylene Glycol | Butylene Glycol | 5.00 |
| Sodium PCA (50%) | Sodium PCA | 2.00 |
| Mica | Mica | 2.00 |
| Isododecane | Isododecane | 10.00 |
| Isononyl Isononanoate | Isononyl Isononanoate | 8.00 |
| Finester 2009 | Polyglycerol Lauroyl Lactylate | 5.00 |
| Finester LAN-S | Glyceryl Hydroxystearate, Glyceryl Adipate, Glyceryl Stearate | 3.00 |
| Caprylyl Methicone | Caprylyl Methicone | 3.00 |
| Finester 6080 | Sorbitan Monooleate | 2.00 |
| Titanium Dioxide 3328 | Titanium Dioxide | 10.00 |
| Gransil PC-12 | Isododecane (and) Polysilicone-11 | 10.00 |
| Diocide | Caprylyl Glycol, Phenoxyethanol, Hexylene Glycol | 1.00 |
| Red Iron Oxide | Iron Oxide | 0.35 |
| Yellow Iron Oxide | Iron Oxide | 0.70 |
| Black Iron Oxide | Iron Oxide | 0.20 |
| | | 100.00 |

Weigh water in main vessel, dissolve butylene glycol, sodium PCA and disperse mica. Homogenize until uniform. Add isododecane, isononyl isononanoate, Finester 2009, Finester LAN-S, Finester 6080, Caprylyl Methicone, titanium dioxide3328 in separate vessel. Homogenize until uniform and add to main vessel with homogenization. While continuing to homogenize add gransil PC-12, red iron oxide, yellow iron oxide, black iron oxide. Homogenize until completely uniform. Add diocide.

7

Example 6: Finester 2009 Study for Counter Irritancy Using Semi-Occlusive Patch Test to Test Skin Irritation/Sensitization

| INCI* | KL5-47/1 | | KL5-47/2 | |
|---|---|---|---|---|
| | % (w/w) | Surfactant Activity | % (w/w) | Surfactant Activity |
| Sodium Laureth Sulfate | 30.00 | 8.40 | 30.00 | 8.40 |
| Polyglycerin-3 (and) Polyglyceryl-3 Lactate/ Laurate (Finester 2009) | X | | 5.00 | 5.00 |
| Phenoxyethanol, Caprylyl Glycol, Hexylene Glycol (Diocide) | 1.00 | | 1.00 | |
| Deionized Water | 69.00 | | 64.00 | |
| Total Active Surfactant | | 8.40 | | 13.40 |

As a control a 30% solution of a common commercial sodium laureth sulfate was prepared. This is a common use level, yielding 8.4% active surfactant.

The test material KL5-47/2 has 5% Finester 2009 in addition to the identical level of sodium laureth sulfate and is found to be extremely mild even in the presence of a known irritant sodium laureth sulfate.

I claim:
1. A personal care composition comprising:
   (a) a polyglycerol ester comprising a reaction product of 5 weight parts of lactic acid, 5 weight parts of lauric acid and 90 weight parts of polyglycerol;
   (b) one or more ingredient(s) and
   (c) water;
   wherein the polyglycerol has an average polymeric degree of 2-5.
2. The personal care composition as claimed in claim 1 wherein (a) is 5 to 50% by weight, (b) is 5 to 50% by weight and (c) is 10 to 90% by weight.

3. The personal care composition as claimed in claim 1 wherein the composition is sulfate free, amide free, ethylene oxide free, silicone free, paraben free and formaldehyde free.

4. The personal care composition as claimed in claim 1 wherein the composition is provided as a shampoo, scalp cleanser, hair cleanser, shower preparation, shower gel, foam bath, gel, body wash, facial cleanser, face wash, makeup remover, cleansing wipe, sunscreen, or foundation.

5. A personal care composition as claimed in claim 1 wherein the polyglycerol comprises 20-40% by weight of diglycerol, 30-50% by weight of triglycerol, 5-15% by weight of tetraglycerol and 2-5% by weight pentaglycerol.

6. The personal care composition as claimed in claim 1 wherein an average molecular weight of polyglycerol is 180-250 g/mol.

7. The personal care composition as claimed in claim 1 wherein polyglycerol ester has a hydroxyl value of 900 to 1200 mg/KOH/gm.

8. The personal care composition as claimed in claim 1 wherein the polyglycerol ester has an HLB value of 15-20.

9. The personal care composition as claimed in claim 1 wherein the one or more ingredient(s) are anionic, cationic, zwiterrionic, nonionic, amphoteric surfactants, superfatting agents, stabilizers, biogenic active ingredients, humectants, preservatives, pearlizing agents, dyes, pigments, fragrances, solvents, opacifiers, thickeners, dispersants, protein derivatives, gelatin, collagen hydrolysates, polypeptides, fatty alcohols, odor masking agents, enzymes, or a combination thereof.

10. A process for preparing the polyglycerol ester as claimed in claim 1 comprising reacting the polyglycerol with the lauric acid and the lactic acid and wherein the polyglycerol comprises 20-40% by weight of diglycerol, 30-50% by weight of triglycerol, 5-15% by weight of tetraglycerol and 2-5% by weight pentaglycerol.

11. A process for preparing the personal care composition as claimed in claim 1 comprising mixing the polyglycerol ester and the one or more ingredient(s) in the water.

* * * * *